(12) United States Patent
Tripathy et al.

(10) Patent No.: US 10,837,935 B2
(45) Date of Patent: Nov. 17, 2020

(54) GAS SENSOR

(71) Applicant: Sciosense B.V., AE Eindhoven (NL)

(72) Inventors: Sanjeeb Tripathy, Cambridge (GB); Wolfram Simmendinger, Burladingen (DE)

(73) Assignee: SCIOSENSE B.V., AE Eindhoven (NL)

( * ) Notice: Subject to any disclaimer, the term of this patent is extended or adjusted under 35 U.S.C. 154(b) by 284 days.

(21) Appl. No.: 15/918,143

(22) Filed: Mar. 12, 2018

(65) Prior Publication Data
US 2019/0277791 A1 Sep. 12, 2019

(51) Int. Cl.
*G01N 27/22* (2006.01)
*G01N 33/00* (2006.01)
*G01N 27/12* (2006.01)

(52) U.S. Cl.
CPC ......... *G01N 27/227* (2013.01); *G01N 27/125* (2013.01); *G01N 27/221* (2013.01); *G01N 33/0037* (2013.01); *G01N 27/128* (2013.01); *G01N 2027/222* (2013.01)

(58) Field of Classification Search
USPC ......................................................... 73/31.05
See application file for complete search history.

(56) References Cited

U.S. PATENT DOCUMENTS

| 4,399,424 A * | 8/1983 | Rigby | G01N 27/12 338/308 |
| 6,047,544 A | 4/2000 | Yamamoto | |
| 6,071,476 A | 6/2000 | Young | |
| 7,849,727 B2 * | 12/2010 | Gardner | G01N 33/0031 73/31.06 |
| 8,043,566 B2 | 10/2011 | Morris | |
| 8,101,448 B2 * | 1/2012 | Renna | B81C 1/00158 257/E21.573 |
| 8,573,030 B2 * | 11/2013 | Gole | G01N 27/127 324/649 |
| 2003/0217586 A1 * | 11/2003 | Gouma | G01N 27/12 73/31.06 |
| 2010/0077840 A1 * | 4/2010 | Srivastava | G01N 27/305 73/31.05 |
| 2011/0086221 A1 * | 4/2011 | Pokorny | C09J 7/29 428/336 |
| 2017/0138879 A1 * | 5/2017 | Akiyama | G01N 27/129 |
| 2017/0276627 A1 | 9/2017 | Dobrokhotov et al. | |
| 2018/0031507 A1 | 2/2018 | Krauss | |
| 2019/0041346 A1 * | 2/2019 | Stacey | G01N 27/128 |

FOREIGN PATENT DOCUMENTS

| CN | 1746131 A | 3/2006 |
| CN | 104820068 A | 8/2015 |
| DE | 3024449 A1 | 1/1982 |
| GB | 2085168 A | 4/1982 |

OTHER PUBLICATIONS

International Search Report and Written Opinion for corresponding Application No. PCT/GB2019/050688, dated May 28, 2019, 16 pages.

* cited by examiner

*Primary Examiner* — Clayton E. LaBalle
*Assistant Examiner* — Warren K Fenwick
(74) *Attorney, Agent, or Firm* — Slater Matsil, LLP

(57) ABSTRACT

We disclose herein a sensing device comprising a substrate, a dielectric layer located on the substrate, a heater located within the dielectric layer; a material for sensing a gas. The material comprises an alumina ($Al_2O_3$) doped conductive metal oxide.

15 Claims, 3 Drawing Sheets

GAS SENSOR

TECHNICAL FIELD OF THE DISCLOSURE

The disclosure relates to gas sensors, particularly but not exclusively, to metal oxide gas sensors for low concentration $NO_2$ detection at a low temperature.

BACKGROUND OF THE DISCLOSURE

Metal oxide (MOX) gas sensors are generally based on the deposition of a metal oxide film onto sensing electrodes defined on or within a suitable substrate. The substrate could be a ceramic or, more recently, a silicon substrate. The deposition process could use a thin film technology, such as sputtering, atomic layer deposition or chemical vapour deposition, or a thick film technology such as screen printing, drop coating, or ink jetting. In the latter case the film could be deposited in the form of an ink or paste where metal oxide grains are held in suspension in a suitable vehicle, often comprising of organic solvents. This vehicle generally needs to be driven off the powder and any organic compounds decomposed to leave an uncontaminated metal oxide. Furthermore, the metal oxide grains generally need to be "fired" to form a mechanically robust, stable, and porous structure which adheres to the substrate and the sensing electrodes.

It has been demonstrated to use Tin Oxide ($SnO_2$) based gas sensors for various applications, especially for Volatile Organic Compounds (VoC) detection. Metal Oxide (MOX) gas sensors are cheap, reliable, easy to fabricate and tunable to various target gases by modifying the functionality of the MOX by adding various noble metal elements (Pd, Pt, Au, Ru, etc.), as well as adding other MOXs in very low concentrations.

Earlier methods of detecting $NO_2$ on a Metal Oxide (MOX) platform were carried out by controlling the properties of a Tungsten Oxide ($WO_3$) based material with various noble metal catalyst additions. These $NO_2$ sensors operate at high temperatures (>350° C.) and are substantially cross sensitive to various other VoCs present in the environment.

Previously demonstrated $NO_2$ sensors have the following disadvantages:
i) detection of low concentrations of $NO_2$ is very difficult;
ii) the sensors must operate at high temperatures (>350° C.). This increases the power consumption and efficiency of the gas sensors;
iii) the noble metals added to the MOXs may react with oxygen or humidity, this introduces a base line instability;
iv) the sensors are sensitive to VoCs;
v) the sensors have a high base line resistance (the resistance in the absence of any oxidizing/reducing gases) at >5 MΩ. This leads to a difficulty in the ASIC design in having a proper sensor output for the user; and
vi) as current transducers include noble metal doped MOX as the sensing element, Siloxane can be produced during operation. This can poison the sensor.

CN104820068 and CN1746131 relate to gas sensors using noble metal (e.g. platinum) doped metal oxides. U.S. Pat. No. 8,043,566 relates to a multi-component gas system using chemical sensors. U.S. Pat. No. 6,071,476 relates to an exhaust gas sensor having a sensing element with a catalytic layer, and U.S. Pat. No. 6,047,544 relates to catalyst unit for purifying the exhaust gas of an engine.

SUMMARY OF THE DISCLOSURE

This disclosure relates to the detection of low concentrations of $NO_2$ (as low as 50 ppb) by doping a metal oxide material (e.g. $SnO_2$) with a low concentration of $Al_2O_3$ (<3%) in using solid state doping technique. Preferably, alumina ($Al_2O_3$) is doped in $SnO_2$ to achieve the desired $NO_2$ detection. This allows detection of $NO_2$ at a heater temperature of 200° C. Cross sensitivity of the disclosed sensor to various VoCs is substantially reduced. The transducer is very selective to $NO_2$ amongst all the gases present in the ambient.

Compared to state-of-the-art sensing devices, the sensing device disclosed will have the following advantages:
i) The sensor can operate at a comparably low temperature, at about 200° C.
ii) There is reduced or no cross sensitivity to VOCs.
iii) The sensor base resistance is in the range of few KO. This simplifies ASIC design and improves the sensor output for the user.
iv) There is a substantially reduced probability of sensor poisoning due to the presence of Siloxane. This because the gas sensing device of the present disclosure does not use noble metals and has a low operating temperature.

According to one aspect of the present disclosure, there is provided a sensing device comprising: a substrate; a dielectric layer located on the substrate; a heater located within the dielectric layer; and a material for sensing a gas, wherein the material comprises an alumina ($Al_2O_3$) doped conductive metal oxide. In other words, the metal oxide material is doped with alumina at a predetermined concentration.

When the material for sensing a gas is exposed to a gas at a particular temperature controlled by the heater, a reaction or diffusion of the gas occurs modifying the electrical properties such as resistance (or capacitance) of the material for sensing a gas.

This has the advantage of providing a sensing device with high sensitivity to gases at low concentrations, at a low device operating temperature. There is a reduced or no cross sensitivity to VoCs, and reduced Siloxane poisoning as there is no requirement for noble metals to be used in the device.

The sensing device may be an $NO_2$ sensing device.

Optionally, the conductive metal oxide may be tin oxide ($SnO_2$). This achieves the desired $NO_2$ detection.

Alternatively, the conductive metal oxide may be any one of a group comprising tungsten oxide, zinc oxide, indium oxide, titanium oxide, chromium oxide, and copper oxide. There is no requirement for noble metals to be used in the device, there is a reduction in device poisoning due to siloxanes, and the device has reduced base line instability. In state-of-the-art device noble metals can react with humidity or oxygen introducing base line instability.

The conductive metal oxide may comprise a combination of said metal oxides. Different metal oxides may be sensitive to different gases or have greater sensitivity at different temperatures. This allows selective detection of gases.

The alumina doping concentration may be between 1% and 10% within the conductive metal oxide.

Preferably, the alumina doping concentration may be between 2.6% and 3% (within the conductive metal oxide). This low doping concentration achieves the desired $NO_2$ detection.

The material for sensing a gas may be highly selective to $NO_2$. This allows detection of $NO_2$ at low concentrations.

The capacitance and/or resistance of the material for sensing a gas may be sensitive to the presence of a gas. Advantageously, this allows detection of a gas by measuring the capacitance and/or resistance of the material for sensing a gas.

The heater may have an interdigitated configuration.

According to a further aspect of the disclosure, there is also provided a sensing device as described above, wherein the substrate may comprise an etched portion and a substrate portion; the dielectric layer may comprise a dielectric membrane, and the dielectric membrane may be adjacent to the etched portion of the substrate; and the heater may be located within the dielectric membrane. The use of the dielectric membrane provides thermal isolation for the heater, and enables the gas sensing device to operate in high temperatures.

The membrane may be formed by back etching the supporting semiconductor substrate. The membrane cavity may either have near vertical sidewalls (formed by the used of Deep Reactive Ion Etching (DRIE)), or may have sloping sidewalls (formed by the used of anisotropic or crystallographic etching methods such as potassium hydroxide (KOH) or TetraMethyl Ammonium Hydroxide (TMAH)). Alternately, the membrane can be formed by a front side etch.

The material for sensing a gas may be located on one side of the dielectric membrane.

According to a further aspect of the disclosure, there is also provided a sensing array device comprising a two dimensional array of a plurality of sensing devices as described above.

The sensing array device may comprise at least one sensing device comprising a material for sensing a gas comprising an alumina doped metal oxide wherein the metal oxide is a first metal oxide; and at least one sensing device comprising a material for sensing a gas comprising an alumina doped metal oxide wherein the metal oxide is a second metal oxide. The first metal oxide and second metal oxide may be different metal oxides. This has the advantage that the first metal oxide and second metal oxide may be sensitive to different gases. This allows a device for sensing more than one gas, and selective detection of gases.

The sensing device may be configured to operate at a temperature of approximately 200° C. This has the advantage of the sensing device having a low power consumption and greater efficiency than state-of-the-art sensing devices. This low operating temperature also reduces the presence of siloxanes in the device and therefore reduces the probably of the sensing device being poisoned by siloxanes.

The sensing device may further comprise an electrode underneath the gas sensing material. The electrode may be configured to measure the resistance and/or capacitance of the gas sensing material. This measurement is dependent on the presence of a gas in the sensing device and therefore is used to detect a gas.

The sensing device may be a CMOS based micro-hotplate in which the heater comprises a CMOS interconnect metal and the dielectric layer comprises a CMOS dielectric layer. CMOS technology offers many advantages such as low fabrication cost in high volume, possibility of circuit integration on the same chip, and good reproducibility from device to device.

The sensing device may further comprise a passivation layer to protect the device.

According to a further aspect of the disclosure, there is provided a method of sensing a gas using the sensing device as described above, the method comprising:
measuring a value of capacitance and/or resistance of the material for sensing a gas, wherein the material comprises an alumina ($Al_2O_3$) doped conductive metal oxide.

According to a further aspect of the disclosure, there is also provided a method of manufacturing a sensing device, the method comprising:
forming a substrate;
forming a dielectric layer disposed on the substrate;
forming a heater within the dielectric layer; and
forming a material for sensing a gas, wherein the material comprises an alumina ($Al_2O_3$) doped conductive metal oxide.

The conductive metal oxide may be any one of a group comprising tin oxide, tungsten oxide, zinc oxide, indium oxide, titanium oxide, chromium oxide, and copper oxide.

BRIEF DESCRIPTION OF THE PREFERRED EMBODIMENTS

Some preferred embodiments of the disclosure will now be described by way of example only and with reference to the accompanying drawings, in which.

DETAILED DESCRIPTION OF THE PREFERRED EMBODIMENTS

Generally speaking, the disclosure relates to gas sensing devices, including a gas sensing material comprising an alumina ($Al_2O_3$) doped metal oxide. This allows improved sensitivity to specific gases in the environment, e.g. $NO_2$, at a reduced sensor operating temperature. It will be understood that the gas sensing material is a powder and a material vehicle mixed together. When it is exposed to a sufficiently high temperature the material formulation can transform into a porous sensing structure or a sensing layer, which is referred to as the gas sensing material. Generally speaking, the metal oxide material is formed from a formulation comprising metal oxide powder (particulate) and a vehicle solvent. When the metal oxide powder and vehicle solvent is mixed together it forms a paste/ink which is then deposited over a sensing electrode. After the deposition, at a high temperature (e.g. about 300° C.), the vehicle solvent is evaporated and/or decomposed from the ink/paste. This is then followed by a ramp to a higher temperature, for example about 600° C., which forms a stable, porous sensing material including metal oxide. In this disclosure, the sensing material is doped with alumina ($Al_2O_3$) for $NO_2$ detection.

Figure 1:
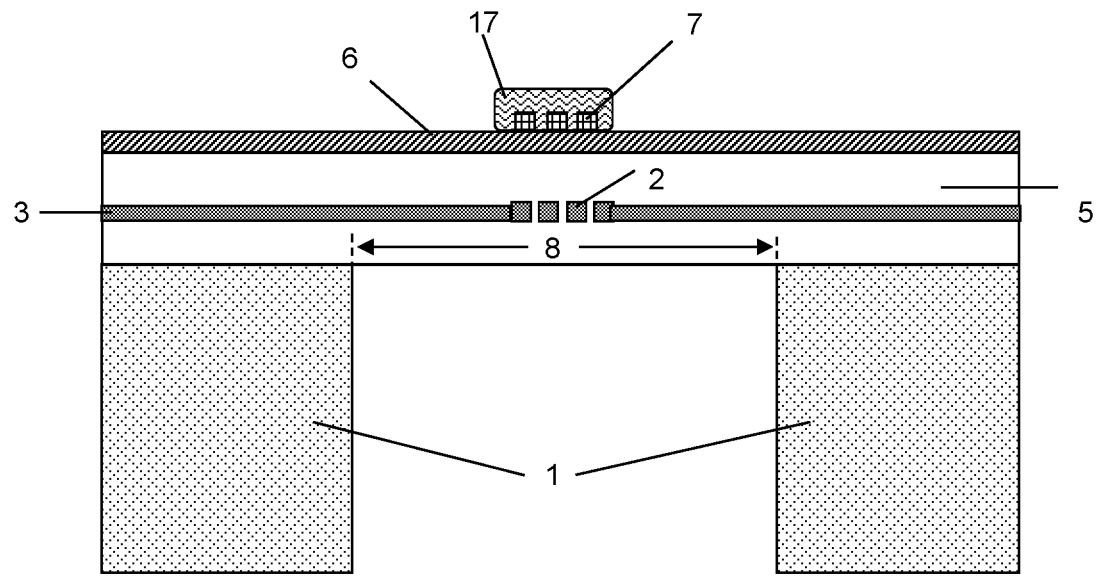
FIG. 1 shows a cross section of a gas sensor with an $Al_2O_3$ doped metal oxide gas sensing material.

FIG. 1 shows a cross section of a gas sensor with an $Al_2O_3$ doped metal oxide gas sensing material. The gas sensor comprises a dielectric membrane 8 supported by a semiconductor substrate 1 which has an etched portion and a substrate portion. Generally speaking, the dielectric membrane area 8 is immediately adjacent to the etched portion of the substrate 1. The dielectric membrane area 8 corresponds to the area above the cavity of the substrate 1. The heater 2 and heater tracks (or metallization) 3 are embedded within the dielectric layer 5, wherein the heater 2 is formed within the dielectric membrane area 8. Electrodes 7 are formed on top of the dielectric membrane 8. The electrodes 7 connect to a gas sensing material 17 which has been grown or deposited on the membrane 8. A passivation layer 6 is formed on top of the dielectric layer 5.

The gas sensing material 17 is disposed on the electrode 7. The electrode 7 is configured to measure resistance and/or capacitance of the gas sensing material 17.

The gas sensing material 17 can be alumina ($Al_2O_3$) doped tin oxide ($SnO_2$). Alternatively the gas sensing material can be an $Al_2O_3$ doped metal oxide such as tungsten oxide ($WO_3$), zinc oxide (ZnO), indium oxide ($In_2O_3$), titanium oxide (TiO), or copper oxide (CuO). The doping concentration is a low doping concentration using a solid state doping technique. The doping concentration is preferably between 2.6% to 3% $Al_2O_3$, however the doping concentration can be anywhere between 1% and 10% $Al_2O_3$ within the metal oxide material.

The sensing material 17 allows the detection of nitrogen dioxide ($NO_2$) at low concentrations. The gas sensor can detect $NO_2$ at concentrations as low as, for example, 50 parts per billion (ppb), due to the low concentration alumina doping of the metal oxide gas sensing material. At a temperature of around 200° C. the gas sensor is highly selective to $NO_2$. Around this temperature the gas sensor has a low sensitivity to other Volatile Organic Compounds (VoC) and reducing gases present. As the gas sensing material does not comprise noble metals, and the gas sensor has a low operating temperature, the gas sensor has a reduced probability of poisoning due to Siloxane.

Figure 2:
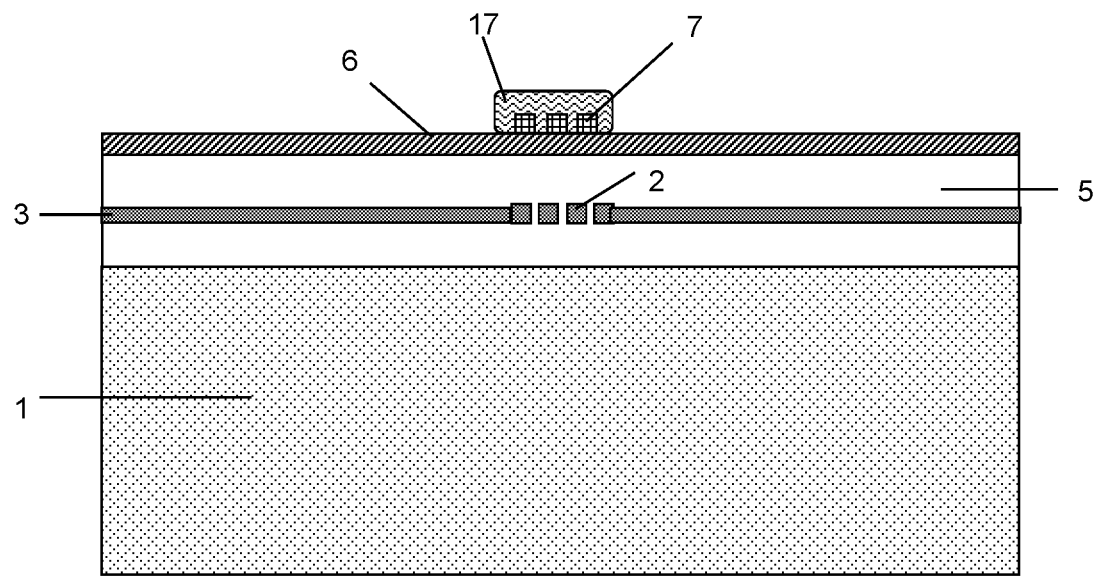
FIG. 2 shows a cross section of an alternative gas sensor with an $Al_2O_3$ doped metal oxide gas sensing material, in which the substrate does not have an etched portion.

FIG. 2 shows a cross section of an alternative gas sensor with an $Al_2O_3$ doped metal oxide gas sensing material. Many of the features of FIG. 2 are similar to those of FIG. 1 and therefore carry the same reference numerals. In this embodiment, the substrate 1 does not have an etched portion. The dielectric layer 5 does not have a dielectric membrane. The heater 2 and heater tracks (or metallization) 3 are embedded within the dielectric layer 5. Electrodes 7 are formed on top of the dielectric layer 5. The electrodes 7 connect to a gas sensing material 17 which has been grown or deposited on the dielectric layer 5. A passivation layer 6 is formed on top of the dielectric layer 5.

Figure 3:
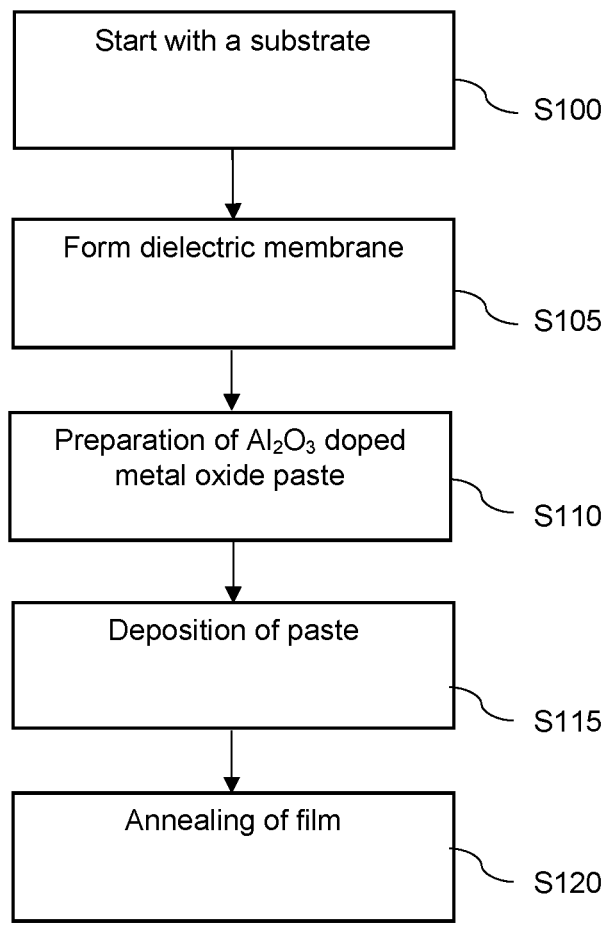
FIG. 3 illustrates an exemplary flow diagram outlining the manufacturing method of the gas sensor.

FIG. 3 illustrates a flow diagram outlining the manufacturing method of the gas sensor. The steps are as follows:
1. In S100, begin with a semiconductor substrate. The substrate comprises an etched portion and a substrate portion. In an alternative embodiment, the substrate is not etched.
2. In S105, form a dielectric layer on the substrate. The dielectric layer comprises a dielectric membrane adjacent to the etched portion of the substrate. A heater is formed within the dielectric membrane. Alternatively, the heater is formed in the dielectric layer on the substrate.
3. In S110, $Al_2O_3$ doped metal oxide powder is formed using solid state powder synthesis. The powder is calcined at 700° C. for 4 hours to obtain the controlled grain size suitable for the $NO_2$ detection and stability. A paste is made from the powder, by for example 40% solid loading of the vehicle.
4. In S115, the paste is deposited at 100° C. onto the dielectric membrane using an ink jet printer with a spot size of, for example, 220 microns.
5. In S120, the film is annealed electrically at 700° C. for 2 hours to obtain the desired texture of the film. This is followed by a gas test at various temperatures to optimize the sensor drive mode.

In S110 the $Al_2O_3$ doped metal oxide powder is formed using solid state powder synthesis. The steps for this are as follows:
  Precursor gel is precipitated from $SnCl_4$ and ammonia solution. For this Tin tetrachloride ($SnCl_4$, extra pure) is hydrolyzed with water, the precursor gel is obtained by mixing the hydrolyzate with ammonia solution (extra pure).
  The mixture is washed repeatedly with deionized water to remove unwanted chloride and ammonium ions.
  The $SnO_2$ content of this gel is determined by thermal gravimetric analysis.
  With this result, the needed amount of alumina is calculated and the respective amount of aluminum nitrate ($Al(NO_3)_3$, extra pure) is weighted out.
  The aluminum nitrate $Al(NO_3)_3$ is dissolved in deionized water.
  The $Al(NO_3)_3$ solution is mixed with the stoichiometric amount of ammonia solution to obtain a white precipitate
  This gel is washed with deionized water to remove unwanted nitrate and ammonium ions.
  Both precipitated gels are mixed for 30 min with a stirrer
  This is followed by drying at 150° C. overnight in a drying oven to obtain white crystals
  The white crystals are (wet) ground thoroughly in a mortar for 15 min.
  This powder is calcined at 800° C. for several hours in a tube furnace under ambient atmosphere, to result in a white powder.

Figure 4:
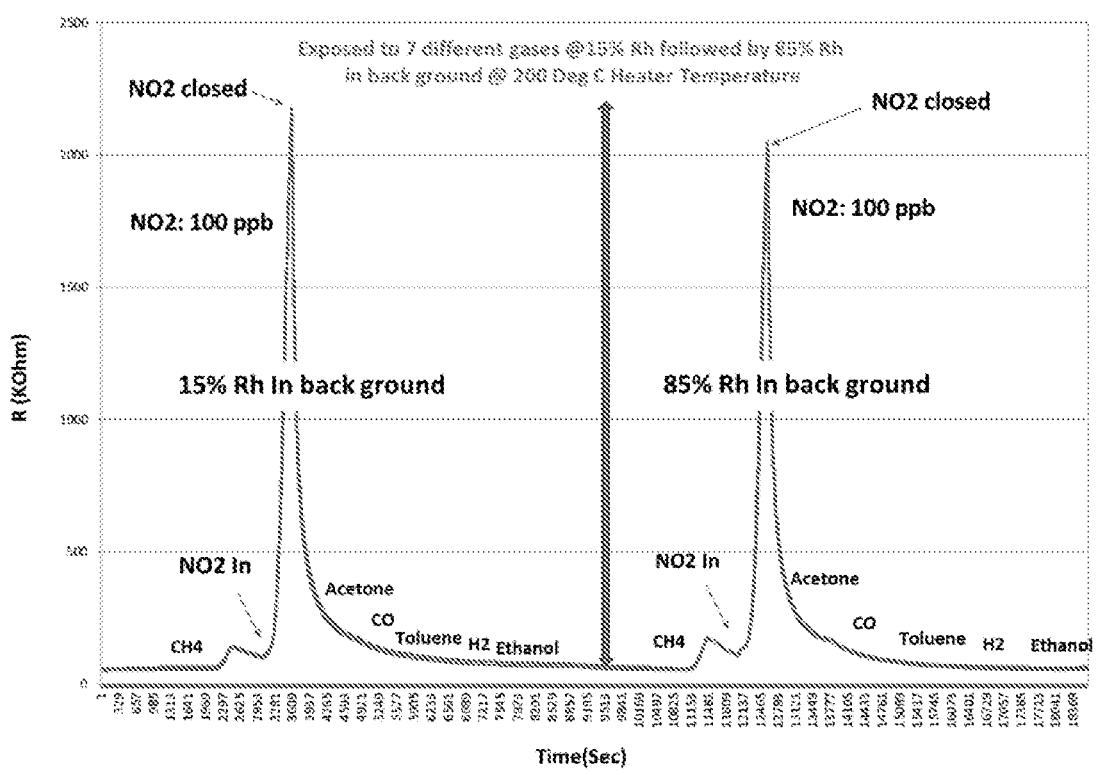
FIG. 4 shows results from a gas functionality test on sensors with $Al_2O_3$ doped $SnO_2$.

FIG. 4 shows results from a gas functionality test on sensors with $Al_2O_3$ doped $SnO_2$. Four sensor parts were tested for sensitivity to 7 gases including methane, $NO_2$, acetone, toluene, CO, ethanol, and $H_2$. The tests were done with 15% background relative humidity, and 85% background relative humidity. The results show that at that around 200° C. heater temperature the sensors are highly selective to a very low concentration of $NO_2$ present in the test chamber and are insensitive to the other six gases present. The tests were carried out in the DC mode to understand the sensor behaviour properly. The humidity had little or no effect on both the selectivity of the sensor and the sensitivity of the sensor.

REFERENCE NUMERALS

1. Semiconductor substrate
2. Embedded heater
3. Heater tracks or metallization
5. Dielectric layer
6. Gas permeable layer
7. Electrodes
8. Dielectric membrane area
17. Sensing material The skilled person will understand that in the preceding description and appended claims, positional terms such as 'above', 'overlap', 'under', 'lateral', etc. are made with reference to conceptual illustrations of an apparatus, such as those showing standard cross-sectional perspectives and those shown in the appended drawings. These terms are used for ease of reference but are not intended to be of limiting nature. These terms are therefore to be understood as referring to a device when in an orientation as shown in the accompanying drawings.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

The invention claimed is:

1. A sensing device comprising:
    a substrate;
    a dielectric layer located on the substrate;
    a heater located within the dielectric layer; and
    a material for sensing a gas,
    wherein the material comprises an alumina ($Al_2O_3$) doped conductive metal oxide,
    wherein the sensing device is an $NO_2$ sensing device,
    wherein the conductive metal oxide is any one of the group consisting of tungsten oxide, zinc oxide, indium oxide, titanium oxide, chromium oxide, copper oxide and tin oxide, and
    wherein an alumina doping concentration is between 1% and 10% within the conductive metal oxide.

2. The sensing device according to claim 1, wherein the conductive metal oxide comprises a combination of the metal oxides.

3. The sensing device according to claim 1, wherein the alumina doping concentration is between 2.6% and 3% within the conductive metal oxide.

4. The sensing device according to claim 1, wherein a capacitance and/or a resistance of the material for sensing a gas is sensitive to a presence of a gas.

5. The sensing device according to claim 1, wherein the heater has an interdigitated configuration.

6. The sensing device according to claim 1,
    wherein the substrate comprises an etched portion and a substrate portion,
    wherein the dielectric layer comprises a dielectric membrane,
    wherein the dielectric membrane is adjacent to the etched portion of the substrate; and
    wherein the heater is located within the dielectric membrane.

7. The sensing device according to claim 6, wherein the material for sensing a gas is located in one side of the dielectric membrane.

8. A sensing array device comprising:
    a two dimensional array of a plurality of sensing devices according to claim 1.

9. The sensing array device according to claim 8, wherein the sensing array device comprises:
    at least one sensing device comprising a material for sensing a gas comprising an alumina doped metal oxide, wherein a metal oxide is a first metal oxide; and
    at least one sensing device comprising a material for sensing a gas comprising an alumina doped metal oxide, wherein a metal oxide is a second metal oxide, and
    wherein the first metal oxide and the second metal oxide are different metal oxides.

10. The sensing device according to claim 1, wherein the sensing device is configured to operate at a temperature of approximately 200° C.

11. The sensing device according to claim 1, further comprising an electrode underneath the material for sensing gas.

12. The sensing device according to claim 11, wherein the electrode is configured to measure a resistance and/or a capacitance of the material for sensing gas.

13. The sensing device according to claim 1, wherein the sensing device is a CMOS based micro-hotplate in which the heater comprises a CMOS interconnect metal and the dielectric layer comprises a CMOS dielectric layer.

14. A method of sensing a gas using the sensing device according to claim 1, the method comprising:
    measuring a value of a capacitance and/or a resistance of the material for sensing a gas, wherein the material comprises an alumina ($Al_2O_3$) doped conductive metal oxide.

15. A method of manufacturing a sensing device, the method comprising:
    forming a substrate;
    forming a dielectric layer disposed on the substrate;
    forming a heater within the dielectric layer; and
    forming a material for sensing a gas,
    wherein the material comprises an alumina ($Al_2O_3$) doped conductive metal oxide,
    wherein the sensing device is an $NO_2$ sensing device,
    wherein the conductive metal oxide is any one of the group consisting of tungsten oxide, zinc oxide, indium oxide, titanium oxide, chromium oxide, copper oxide and tin oxide, and
    wherein an alumina doping concentration is between 1% and 10% within the conductive metal oxide.

* * * * *